(12) United States Patent
Samson et al.

(10) Patent No.: US 6,547,760 B1
(45) Date of Patent: Apr. 15, 2003

(54) AORTIC CATHETER WITH POROUS AORTIC ARCH BALLOON AND METHODS FOR SELECTIVE AORTIC PERFUSION

(75) Inventors: Wilfred J. Samson, Saratoga, CA (US); John A. Macoviak, La Jolla, CA (US)

(73) Assignee: Cardeon Corporation, Cupertino, CA (US)

(*) Notice: Subject to any disclaimer, the term of this patent is extended or adjusted under 35 U.S.C. 154(b) by 0 days.

(21) Appl. No.: 09/366,188

(22) Filed: Aug. 3, 1999

Related U.S. Application Data
(60) Provisional application No. 60/095,523, filed on Aug. 6, 1998.

(51) Int. Cl.$^7$ .............. A61M 31/00; A61M 37/00; A61M 29/00
(52) U.S. Cl. ............ 604/103.01; 604/101.01; 604/606; 606/194
(58) Field of Search ............ 604/96.01, 97.01, 604/98.01, 101.01, 101.05, 102.01–3, 103.06, 264, 523, 103.01, 103.07, 6.16, 915; 606/194, 192

(56) References Cited

U.S. PATENT DOCUMENTS

| | | | |
|---|---|---|---|
| 5,282,785 A | * | 2/1994 | Shapland et al. ............ 604/21 |
| 5,286,254 A | * | 2/1994 | Shapland et al. |
| 5,368,555 A | | 11/1994 | Sussman et al. |
| 5,599,307 A | * | 2/1997 | Bacher et al. ......... 604/101.05 |
| 5,611,775 A | * | 3/1997 | Machold et al. |
| 5,704,908 A | * | 1/1998 | Hofmann et al. ............ 604/21 |
| 5,866,561 A | * | 2/1999 | Ungs |
| 6,267,747 B1 | * | 7/2001 | Samson et al. |

OTHER PUBLICATIONS

David P. Bichell, MD, et al., Axilloaxillary Cardiopulmonary Bypass: A Practical Alternative to Femorofemoral Bypass. © 1997 by The Society of Thoracic Surgeons Published by Elsevier Science Inc., pp. 702–705.

Joseph F. Sabik, MD, et al., Axillery Artery: An Alternative Site of Arterial Cannulation for Patients with Extensive Aortic and Peripheral Vascular Disease, © 1995 by Mosby-Year Book, Inc. The Journal of Thoracic and Cardiovascular Surgery, pp. 886–891.

Nicholas T. Kouchoukos, et al., Perfusion for Thoracic Aortic Surgery, Section V. Clinical Application and Management of CPB, pp. 636–654.

* cited by examiner

*Primary Examiner*—Brian L. Casler
*Assistant Examiner*—Catherine Serke
(74) *Attorney, Agent, or Firm*—Fulwider Patton Lee & Utecht, LLP

(57) ABSTRACT

A method and device for perfusing an organ system is provided. The device may be further described as a catheter or cannula with an expandable flow control member positioned of the distal portion of the catheter shaft. The flow control member has a porous portion, and at least one impermeable portion, which prevent fluid from flowing out the ends of the flow control member. The flow control member is further characterized as having an interior chamber that is in fluid communication with a perfusion lumen that extends along the length of the catheter shaft and is in fluid communication with an external perfusion pump. The perfusion lumen is configured for providing flow to the interior of the flow control member, to create radial expansion thereof and to provide adequate flow to the arch vessels through said porous portion to sustain the metabolic demands of the brain.

36 Claims, 13 Drawing Sheets

AORTIC CATHETER WITH POROUS AORTIC ARCH BALLOON AND METHODS FOR SELECTIVE AORTIC PERFUSION

This application claims the benefit of Provisional application Ser. No. 60/095,523 filed Aug. 6, 1998.

FIELD OF THE INVENTION

The invention relates to a catheter or cannula system that facilitates cardiopulmonary surgeries and enables prolonged circulatory support of the heart. More specifically, the invention relates to an aortic catheter for segmenting and selectively perfusing the aorta during cardiopulmonary bypass.

BACKGROUND OF THE INVENTION

Heart surgery has generally required major open chest surgical procedures that put the patient at risk. Relatively high mortality rates and complications result from such invasive surgeries. Further, the surgeries require extensive hospitalization and recuperation time. Surgical methods to correct heart problems are desirable which do not require open chest approaches. Some surgical techniques have been described for particular applications employing an intra-aortic catheter introduced into the vascular system of the patient.

Recent advances in the field of minimally invasive cardiac surgery have included the development of aortic catheters and methods for inducing cardioplegic arrest without the necessity of opening the patient's chest with a sternotomy or other major thoracotomy. For example, U.S. Pat. No. Re 35,352 to Peters describes a single-balloon catheter for occluding a patient's ascending aorta and a method for inducing cardioplegic arrest. A perfusion lumen or a contralateral arterial cannula is provided for supplying oxygenated blood during cardiopulmonary bypass. U.S. Pat. No. 5,584,803 to Stevens et al. describes a single balloon catheter for inducing cardioplegic arrest and a system for providing cardiopulmonary support during closed chest cardiac surgery. A coaxial arterial cannula is provided for supplying oxygenated blood during cardiopulmonary bypass. The occlusion balloon of these catheters must be very carefully placed in the ascending aorta between the coronary arteries and the arch vessels, therefore the position of the catheter must be continuously monitored to avoid complications.

One difficulty encountered with prior art aortic catheters is the tendency of the single balloon catheters to migrate or drift in the direction of the pressure gradient within the aorta. Specifically, during infusion of cardioplegia, the balloon catheter will tend to drift downstream away from the heart and toward the aortic arch and, when the cardiopulmonary bypass pump is engaged during the procedure, the balloon catheter will tend to drift upstream in the opposite direction toward the heart into the aortic root. This migration can be problematic if the balloon drifts downstream far enough to occlude one or more of the arch vessels, or upstream enough to occlude the coronary arteries, or to pass through the aortic valve into the ventricle.

PCT patent application WO 9721462 by Fan et al. attempts to overcome this problem with a balloon catheter having high friction areas on the outer surface of the balloon. A problem with this single balloon approach is that a relatively large balloon is needed to create enough friction to avoid migration of the inflated balloon. The larger the balloon is, the more carefully it must be placed in the ascending aorta to avoid occluding the coronary arteries or the arch vessels and the less margin of error there is should any balloon migration occur.

Furthermore, what is needed are medical instruments and cannula/catheters for compartmentalizing and selectively perfusing the cerebral circulation with antegrade flow. Such mechanisms are necessary to minimize complications of a vast array that are related to proper management of blood flow in the body. Selective perfusion can be used to prioritize the flow of oxygenated blood or other protective fluids to the various organ systems, therefore achieving optimal preservation of all organ systems within the body.

Furthermore, what is needed is a peripheral access catheter configuration that is more resistant than prior apparatus to migration due to pressure gradients within the patient's aorta.

The following patents, and all other patents referred to herein, are hereby incorporated by reference in their entirety. U.S. Pat. Nos. 5,308,320, 5,383,854, 582,093 and 5,906,588 by Safar et al.; U.S. patent application Ser. No. 08/909,293, filed Jul. 11, 1997, by Safar et al.; U.S. patent application Ser. No. 09/152,589, filed Sep. 11, 1998, by Safar et al.; U.S. Pat. No. 5,738,649, by John A. Macoviak; U.S. patent application Ser. No. 09/060,412 filed Apr. 14, 1998 by Macoviak; U.S. Pat. Nos. 5,833,671, 5,827,237 by John A. Macoviak and Michael Ross; U.S. patent application Ser. No. 08/665,635, filed Jun. 17, 1996, by John A. Macoviak and Michael Ross; and U.S. patent application Ser. No. 09/205,753, filed Dec. 8, 1998, by Bresnahan et al.

SUMMARY OF THE INVENTION

Accordingly, the invention provides a catheter or cannula having a flow control member positioned near the distal end of the catheter for occluding a first body lumen at a point where a second body lumen branches from the first lumen, and for perfusing the branch lumen. The invention will be described more specifically herein relating to an aortic catheter or cannula having an occlusion member positioned in the aortic arch, having a length sufficient to cover the ostia of the arch vessels. The flow control member is intended to fulfill at least one and preferably all four of the following functions: (1) occluding the aorta at the aortic arch, (2) selectively perfusing one or more of the coronary arteries, the arch vessels, or the descending aorta with a selected fluid, (3) providing filtered perfusion to one or more of the coronary arteries, the arch vessels, or the descending aorta, and (4) resisting migration of the distal flow control member and the cannula.

The primary flow control member may be formed in a variety of configurations, but will include a primary flow control member positioned in the aortic lumen, having a length sufficient to cover the ostia of the arch vessels. The flow control member may comprise one or more inflatable balloons or one or more selectively deployable external catheter valves, or a combination of balloons and valves. In embodiments where the primary flow control member is a single inflatable balloon, the flow control member will have at least one permeable or mesh portion. The balloons used, whether porous or nonporous, may be elastic so that they stretch in proportion to the inflation pressure, or may be flaccid or sack-like so that they inflate at low pressure and reach their design diameter quickly. The sack-like balloons may be relatively non-compliant at their design diameter or they may be compliant, exhibiting elastic behavior after initial inflation, e.g. to closely fit the aortic lumen size and curvature.

The catheter may further include one or more auxiliary flow control members located upstream or downstream from the primary flow control member to further segment the patient's circulatory system for selective perfusion to different organ systems or to assist in anchoring the catheter in a desired position. Usable auxiliary flow control members include, but are not limited to, expandable or inflatable members such as inflatable balloons and valves. Examples of various valves may include collapsible/expandable valves including retrograde valves, antegrade valves, and various central flow and peripheral flow valves. In addition, a combination of valves and inflatable members may be used as appropriate for a given procedure. In some embodiments, the catheter body can include one or more antegrade and retrograde valves, as well as one or more inflatable balloons. Inflatable balloons and collapsible/deployable valves have been previously incorporated by reference herein and any desirable or practical inflatable balloon or deployable valve may be used. Inflatable balloons typically include an interior chamber that is in fluid communication with an inflation lumen extending within the catheter shaft from a location from within the respective flow control member to a location in the proximal portion, which is adapted to extend out of the patient.

Preferably, the flow control member, and any auxiliary flow control members, or anchoring members, if present, are mounted on an elongated catheter shaft. In a preferred embodiment, the catheter shaft includes at least one lumen for inflating or otherwise deploying the primary flow control member and for perfusion of the arch vessels with oxygenated blood or other fluids, a lumen for corporeal perfusion, and a guidewire lumen. In alternate embodiments, lumens may be included for deploying the auxiliary flow control members, and for measuring the pressure at desired locations within the aorta. The catheter may be configured for retrograde deployment via a peripheral artery, such as the femoral artery, or it may be configured for antegrade deployment via an aortotomy incision or direct puncture in the ascending aorta.

In some embodiments of the invention, filtration may be an important feature. To capture embolic material without unduly disrupting blood flow, the porous section or sections must have an appropriate combination of characteristics including effective filter surface area and pore size;

the correct combination depending on a number of factors including fluid pressure. For filters comprised of a mesh, the thread diameter is another important characteristic to consider. Typically, the flow rates required in the arch vessels total between 0.5 and 1.5 L/min depending on a variety of factors including the size of the patient and the temperature of the perfusate. Pore size is preferably 500 $\mu$m or less, more preferably 200 $\mu$m or less, and most preferably 50 $\mu$m or less, but larger than at least a red blood cell, although larger pore sizes may be required in some embodiments.

Methods according to the present invention are described using the aortic catheter for occluding and compartmentalizing or partitioning the patient's aortic lumen and for performing selective filtered aortic perfusion.

DETAILED DESCRIPTION OF THE INVENTION

Figure 1:
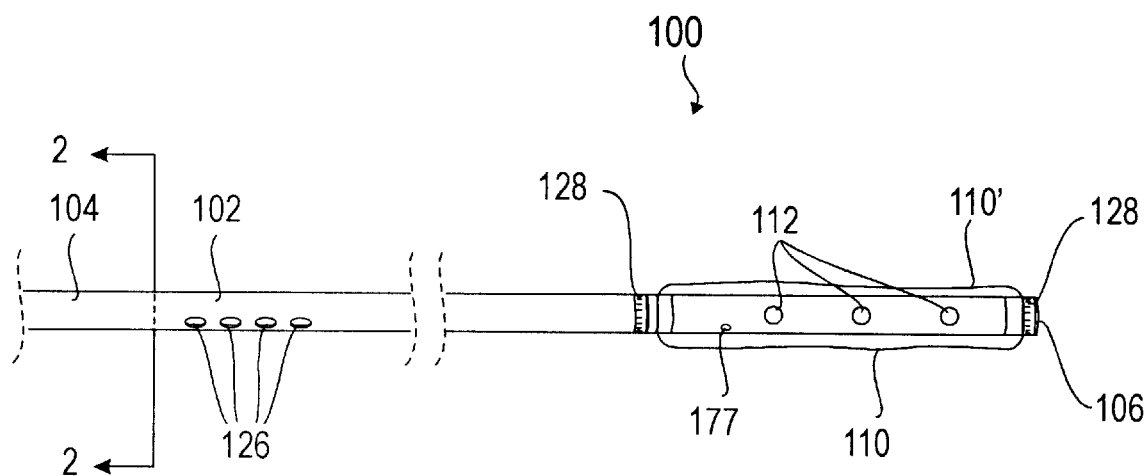
FIG. 1 is a side view of a shaft portion of a first embodiment of the aortic catheter of the present invention having a single-balloon flow control member in the unexpanded state.

Turning now descriptively to the drawings, in which similar reference characters denote similar elements throughout the separate embodiments, the catheter described herein with all of its preferred features represents a versatile device having multiple uses. The invention provides a catheter having a primary flow control member positioned near the distal end of the catheter for occluding a first body lumen at a point where a second body lumen branches from the first body lumen and for perfusing the branch lumen. However, the invention will be described more specifically herein relating to an aortic catheter having a primary flow control member configured to be positioned in the aortic arch and having a length sufficient to cover the ostia of the arch vessels. The primary flow control member may have at least one permeable or mesh portion in fluid communication with the ostia of the arch vessels, and may be an inflatable balloon, or include one or more inflatable balloons, or one or more selectively deployable external catheter valves as subunits thereof, or a combination of balloons and valves as subunits thereof. The catheter is characterized by a flexible catheter shaft placed by surgical cutdown or needle/introducer guidewire technique into the vessels of the lower or upper extremity or neck. Larger internal vessels may also be used. Alternatively, the catheter may be introduced centrally through direct penetration of the ascending aorta.

In some embodiments, filtration may be an important feature of the invention. To filter blood and effectively capture embolic material without unduly disrupting blood flow, the porous section or sections must include an appropriate combination of characteristics including effective filter surface area and pore size, which combination will vary depending on a number of factors including the fluid pressure inside the catheter. For filters comprised of a mesh, the thread diameter is another important characteristic to consider. Typically, the flow rates required in the arch vessels total between 0.5 and 1.5 L/min depending on a variety of factors including the size of the patient and the temperature of the perfusate. Pore size is preferably 500 $\mu$m or less, more preferably 200 $\mu$m or less, and most preferably 50 $\mu$m or less, but larger than at least a red blood cell. However, small filter surface areas disclosed in some embodiments may require larger pore sizes than those given above in order to achieve the necessary rate of flow at an acceptable pressure.

Once appropriate physical characteristics are determined, suitable meshes can be found among standard meshes known in the art. For example, polyester meshes may be used, such as meshes made by Saati Corporations and Tetko, Inc. These are available in sheet form and can be easily cut and formed into a desired shape. Other meshes known in the art, which have the desired characteristics are also suitable.

Anticoagulants or antithrombogenic compounds may be applied to the mesh to reduce the chances of blood clotting on the mesh. The anticoagulants or antithrombogenic compounds may be painted, dipped, sprayed or chemically bonded onto the mesh and/or onto other parts of the catheter or the catheter lumens. Other methods known in the art for applying anticoagulants or antithrombogenic compounds may also be used. Anticoagulants, such as heparin and heparinoids, may be used. Anticoagulants other than heparinoids may also be used, for example monoclonal antibodies such as ReoPro.

Perfusion of blood to the arch vessels will preferably be performed with a pressure drop through the catheter and across the filter of less than approximately 300 mm Hg, more preferably less than approximately 100 mm Hg, in order to reduce hemolysis while providing a blood flow preferably between 0.5 to 1.5 liters per minute. Preferred perfusion pressures may be different for perfusates that do not contain blood and therefore are not subject to hemolysis.

Figure 2:
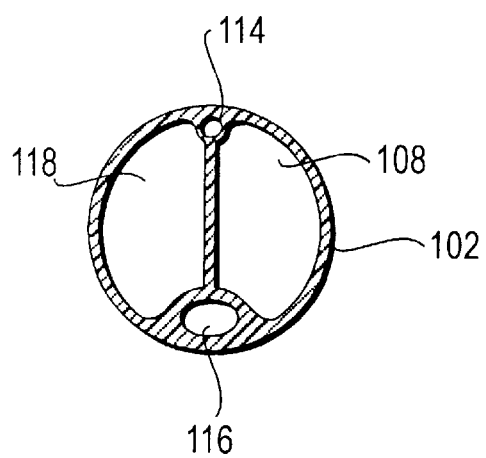
FIG. 2 is a magnified lateral cross section of the aortic catheter shaft of FIG. 1 taken along line 2—2.

FIG. 1 illustrates the shaft portion of a first embodiment of the invention having a primary flow control member 110. FIG. 2 is a magnified lateral cross section of the aortic catheter taken along line 2—2 in FIG. 1. The aortic catheter 100 has an elongated catheter shaft 102 having a proximal portion 104 that preferably extends out of the patient's body, and a distal end 106 adapted to extend into the patient's aorta. The elongated catheter shaft 102 should have an overall length sufficient to reach from the arterial access point where it is inserted into the patient to its deployed position within the aorta. For femoral artery deployment in adult human patients, the elongated catheter shaft 102 preferably has an overall length from approximately 60 cm to 120 cm, and more preferably 70 cm to 90 cm.

Referring to FIG. 2, which is a cross section of the catheter shaft 102 taken along line 2—2 of FIG. 1, the elongated catheter shaft 102 preferably has at least four lumens, an inflation/perfusion lumen 108 that provides blood to the primary flow control member 110 and to the arch vessels through the flow control member perfusion ports 112, a pressure lumen 114 opens to a pressure port 177, a guidewire lumen 116, and a corporeal perfusion lumen 118 that is used to perfuse the descending aorta through the corporeal perfusion ports 126. The configuration of the lumens shown is for illustrative purposes only, and other configurations may be used. For example, in alternate embodiments the catheter shaft 102 may not include a corporeal perfusion lumen 118 or pressure lumen 114 that will help simplify the manufacture of the aortic catheter 100. In configurations where corporeal perfusion is not integrally built into the aortic catheter, corporeal perfusion may be provided by a coaxial, collateral or contralateral arterial cannula. Alternatively, additional lumens may be included such as perfusion lumens, monitoring lumens or validation of catheter placement lumens.

In a preferred embodiment, the elongated catheter shaft 102 has an outer diameter that is preferably approximately 9 to 26 French (3.0 to 8.7 mm), and more preferably 12 to 18 French (4.0 to 6.0 mm) for use in adult human patients. Catheters for pediatric use, or use in non-human subjects, may require different dimensions and would be scaled accordingly. The elongated catheter shaft 102 is preferably formed of a flexible thermoplastic material, a thermoplastic elastomer, or a thermoset elastomer. Suitable materials for use in the elongated catheter include, but are not limited to, polyvinylchloride, polyurethane, polyethylene, polyamides, polyesters, silicone, latex, and alloys or copolymers thereof, as well as braided, coiled or counterwound wire or filament reinforced composites.

The primary flow control member 110, of FIG. 1, is mounted proximal the distal end 106 of the elongated catheter shaft 102 or alternatively may extend beyond the distal end 106. The flow control member 110 is intended to fulfill at least one and preferably all four of the following functions: (1) occluding the aorta at the aortic arch, (2) selectively perfusing one or more of the coronary arteries, the arch vessels, or the descending aorta with a selected fluid, (3) providing filtered perfusion to one or more of the coronary arteries, the arch vessels, or the descending aorta, and (4) resisting migration of the primary flow control member 110 or cannula 100.

Figure 3:
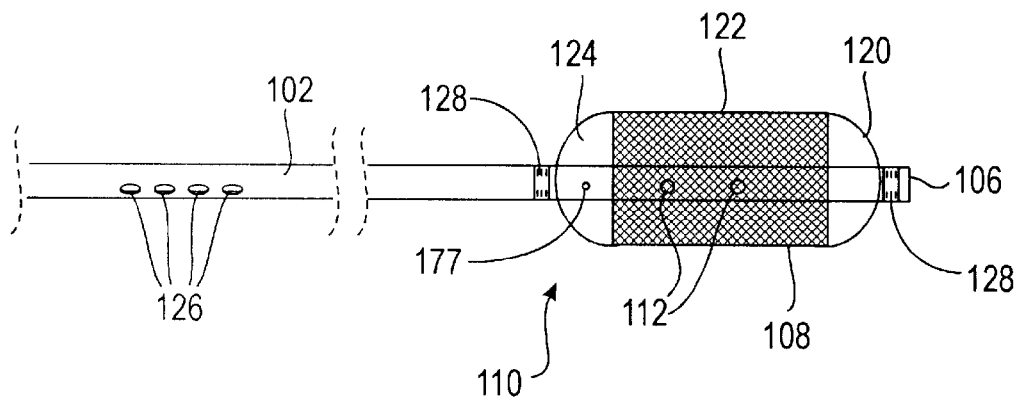
FIG. 3 is a side view of the flow control member of the aortic catheter of FIG. 1 showing a single-balloon flow control member in a deployed or expanded state.

FIG. 3 illustrates the flow control member 110 of FIG. 1 in the expanded or deployed position. The expandable flow control member may be mounted to the exterior of the catheter shaft by heat bonding, heat welding, with an adhesive or by mechanical or frictional means. The flow control member 110 comprises a balloon having a distal end 120, a middle portion 122, and a proximal end 124. The distal end 120 and the proximal end 124 are preferably formed of a nonporous material creating at least one occlusive end, while the middle portion is preferably formed of a mesh or porous material. The inflatable flow control member 110 has a deflated state 110' as illustrated with reference to FIG. 1, in which the diameter of the flow control member is, preferably, not substantially larger than the diameter of the catheter shaft 102 and an inflated state 108 in which the flow control member 110 expands to a diameter sufficient to at least partially occlude blood flow in the aortic arch of a patient. For use in adult humans, the flow control member 110 preferably has an inflated outer diameter of approximately 1 to 7 cm more preferable 2 to 5 cm. When the primary flow control member 110 comprises an inflatable balloon, whether porous or nonporous, the inflatable balloon may be elastic so that it stretches in proportion to the inflation pressure, or may be flaccid or sack-like so that it inflates at low pressure and reaches its design diameter quickly. The sack-like balloon may be relatively non-compliant at its design diameter or it may be compliant, exhibiting elastic behavior after initial inflation, to closely fit the aortic lumen size and curvature. The material or materials used in the inflatable primary flow control member 110 is preferably characterized by properties that allow an internal pressure within the distal flow control member 110 to be maintained at a sufficient level to occlude the aorta, while also allowing a controlled volume of fluid to escape from the flow control member for perfusing the arch vessels. Suitable materials which may be used for flow control member 110 include polyurethanes, polyethylene terephthalate (PET), polyvinyl chloride (PVC), ethylene vinyl acetate (EVA), latex and polyolefin. Furthermore, the surface of the flow control member may have porous regions that allow a fluid to be perfused at a known rate when a specific pressure is attained while not allowing other porous regions to open until a greater internal pressure in the balloon is attained. For perfusion of the arch vessels, it is preferable that the flow rate provided to the arch vessels be controllable within a range from 0.1 to 2.0 liters per minute, and more preferably within a range from 0.5 to 1.5 liters per minute, depending on a variety of factors. Therefore, the flow control member 110 has material properties that allow for the aforementioned perfusion range while still maintaining occlusion properties when deployed in the aorta.

The porous and nonporous sections of the primary flow control member 110 may be formed from the same or separate materials. Suitable materials for the nonporous portions of the inflatable flow control member 110 include, but are not limited to, elastomers, thermoplastic elastomers, polyvinylchloride, polyurethane, polyethylene, polyamides, polyesters, silicone, latex, and alloys or copolymers, and reinforced composites thereof. In addition, the outer surface of the flow control member 110 may include a force or friction increasing means such as a friction increasing coating or texture to increase friction between the distal flow control member 110 and the aortic wall when deployed. Suitable materials for the mesh or porous middle portion 122 include, but are not limited to, a perforated polymer film, porous or microporous membranes, TYVEK (spun-bonded polyethylene), GORTEX (expanded PTFE), woven or knit mesh or fabric, or the like.

Figure 4:
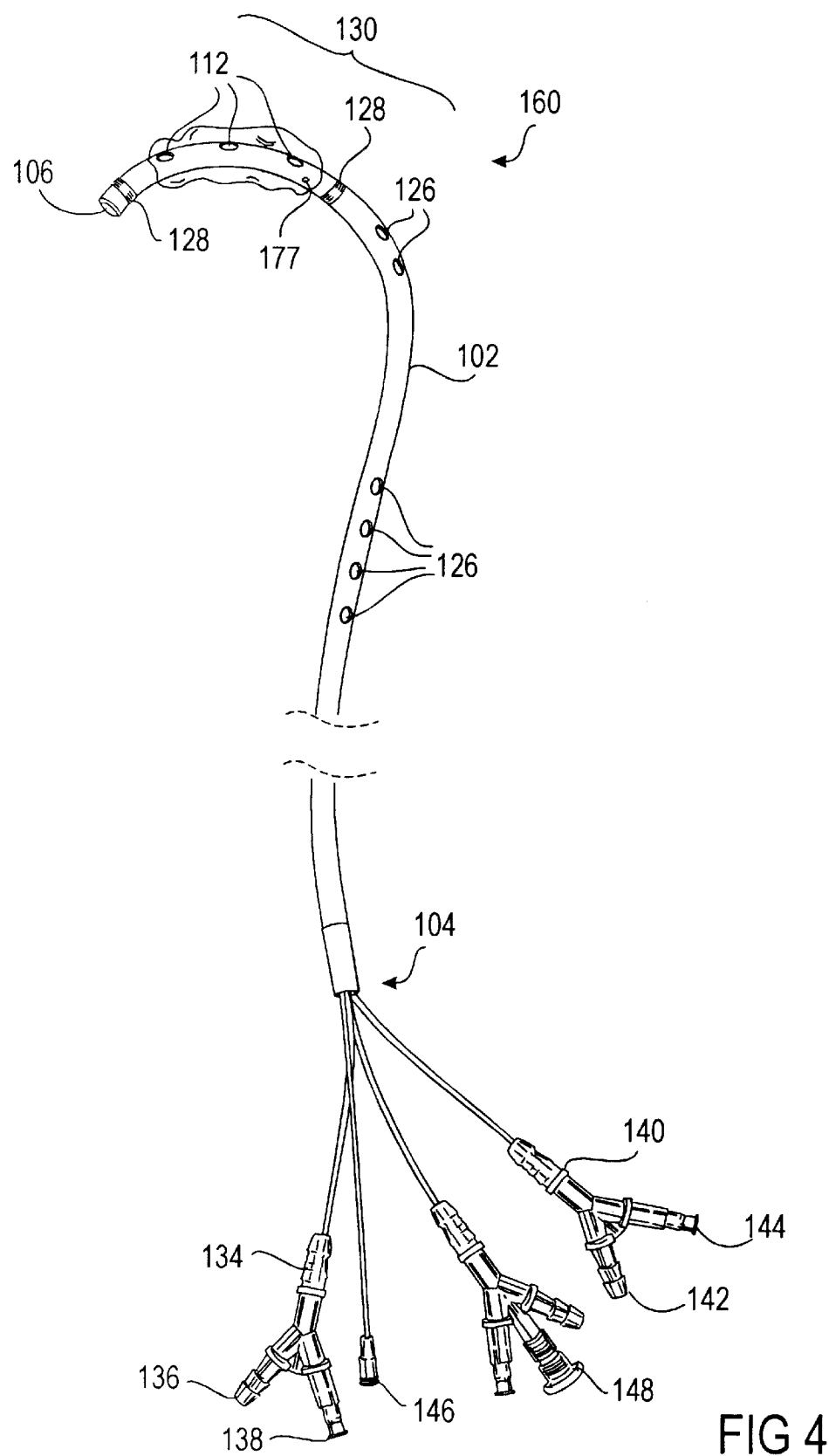
FIG. 4 is a side view of the aortic catheter of FIG. 1 configured for retrograde introduction into a patient's femoral artery and illustrating the manifold connections to the proximal end of the aortic catheter.

Referring now to FIG. 4, to facilitate placement of the catheter 100 within the aorta, and to improve the stability of the catheter 100 in the proper position in the patient's aorta, a distal region 130 of the aortic catheter 100 may be preshaped to conform to the internal curvature of the patient's aortic arch. The distal region 130 represents a J-shaped curve of approximately 180 degrees of arc with a radius of curvature of approximately 2 to 4 centimeters, for use in a typical adult human patient and may be reinforced with polymer filaments or metal or both. The distal end 106 of the aortic catheter 100 may also be skewed slightly out of the plane reflecting the forward angulation of the typical patient's ascending aorta.

The proximal end/portion 104 of the aortic catheter 100 has fittings for each of the catheter lumens 108, 114, 116, and 118. The corporeal perfusion lumen 118 is coupled to a Y-fitting 134 having a barb connector 136 for connection to a perfusion pump or the like, and a luer connector 138 for injecting medications or other fluids. In alternate embodiments, the catheter shaft 102 may further include a pressure lumen coupled to a luer connector for monitoring the corporeal perfusion pressure, withdrawing fluid samples, or for injecting medications or other fluids. The flow control member deployment and perfusion lumen 108 is coupled to a Y-fitting 140 having a barb connector 142 for connection to the same perfusion pump 900 a perfusion pump or the like, and a luer connector 144 for injecting medications or other fluids. The arch pressure lumen 114 is coupled to a luer connector 146 for monitoring the arch perfusion pressure, withdrawing fluid samples, or for injecting medications or other fluids. The guidewire lumen 116 is coupled to a Touhy-Borst fitting 148, or other hemostasis valve. In alternate embodiments having an auxiliary flow control member and where separate lumens are desired for deploying the auxiliary flow control member, additional fittings suitable for connecting to a syringe or other inflation or deployment device would be provided.

Figure 5:
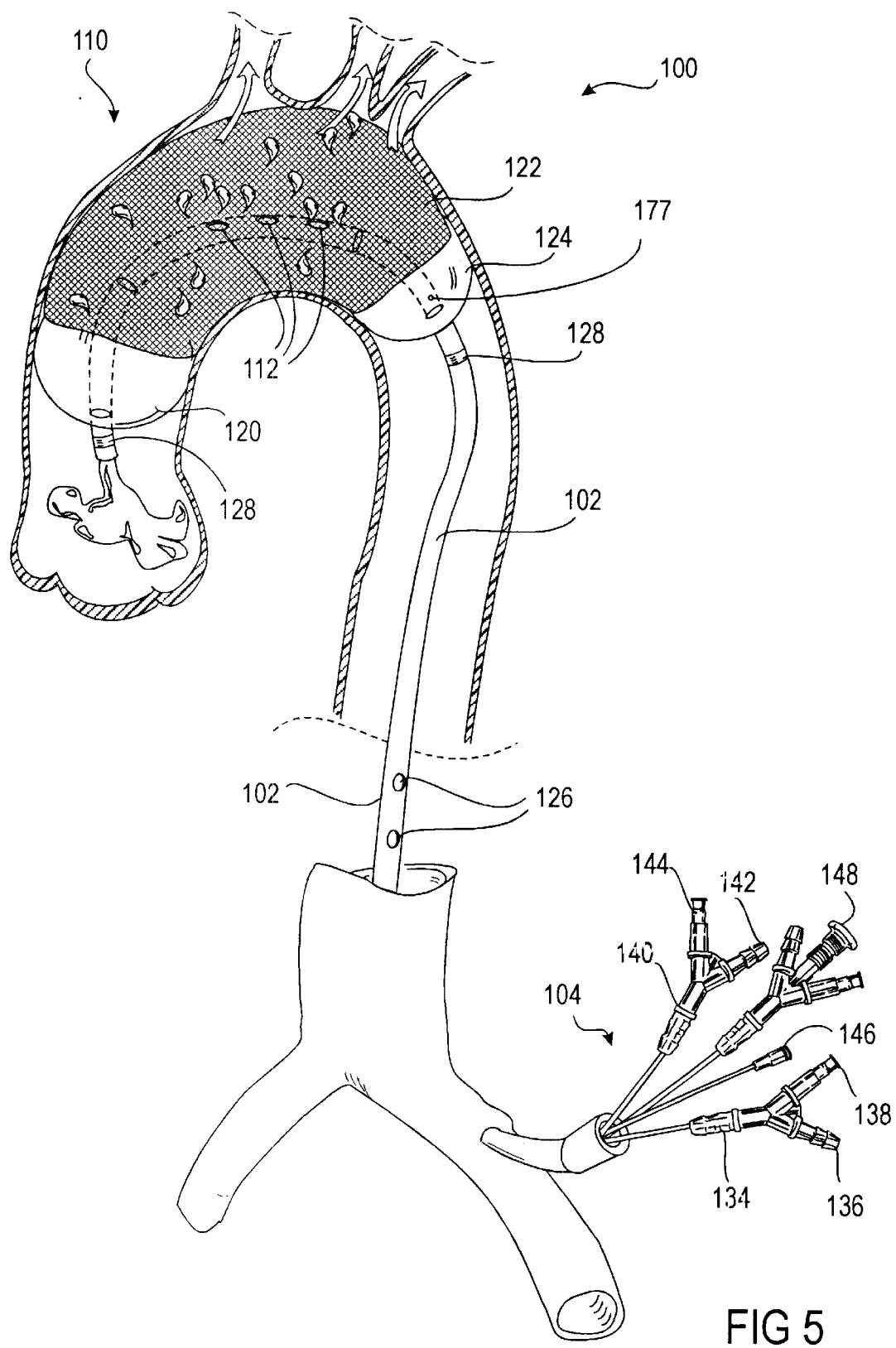
FIG. 5 is a side view of the aortic catheter of FIG. 1 deployed or expanded in an aorta.

Illustrated in FIG. 5 is the flow control member 110 deployed in the aorta illustrating the functional features and material attributes of the control member 110 in use. The flow control member 110 is positioned within the aortic arch with the porous middle portion 122 covering the ostia of the arch vessels. A selected fluid, such as oxygenated normothermic blood, oxygenated hypothermic blood, blood substitutes such as PERFLUBRON or other perfluorocarbon compounds, radiopaque dyes for angiography, or the like, is introduced through the flow control member inflation and perfusion lumen 108 into the inflatable flow control member 110. Some selected fluid may seep out through the porous middle portion 122 during inflation, but at a rate less than the rate at which the selected fluid enters the flow control member 110. In an alternate embodiment, it may be preferable to initially inflate the flow control member 110 with a more viscous solution, for example a radiopaque contrast agent mixed with saline, that will flow through the porous middle portion 122 at a rate slower than the selected perfusion fluid will leak.

When the correct pressure is attained, the flow control member 110 occludes blood flow through the aortic lumen. The selected fluid used to inflate the flow control member 110 may escape through the porous portion 122 at a known rate into the arch vessels. The flow rate may be adjustable by adjusting the pressure within the flow control member 110. Contact with the aortic wall and the middle porous portion 122 of the flow control member 110 will reduce or prevent seepage of the selected fluid through sections of the porous middle portion 122 of the flow control member 110 not aligned with the arch vessels. The middle porous portion 122 of the flow control member 110 contacting the aortic wall may also provided resistance to the migration of the flow control member 110 or cannula 100.

Preferably, the aortic catheter 100 includes one or more location markers 128, such as radiopaque markers and/or sonoreflective markers, to enhance imaging of the aortic catheter 100 during deployment using standard fluoroscopy, ultrasound, MRI, MRA, transesophageal chocardiography, or other techniques. A radiopaque location marker 128 may be formed as a ring or disk of dense radiopaque metal such as gold, platinum, tantalum, tungsten, or compounds or alloys thereof, or a ring of a polymer or adhesive material heavily loaded with a radiopaque filler material.

In use, the catheter 100 is advanced up the descending aorta and across the aortic arch, under fluoroscopic or ultrasound guidance with the aid of a guidewire within the guidewire lumen 116. The aortic catheter 100 is advanced until the primary flow control member 110 is positioned in the aortic arch. This may be determined by reference to the radiopaque marker or markers 128. Using a multihead cardiopulmonary bypass pump or the like, perfusion of oxygenated blood is started through the perfusion ports 112. The flow control member 110 is then inflated to occlude the aortic arch using a selected perfusion fluid such as oxygenated blood. When the correct pressure is achieved, the perfusion fluid flows from the flow control member 110 and enters the arch vessels. The rate of flow of the perfusion fluid may be controlled by adjusting the pressure within the flow control member 110. At the completion of the surgical procedure, the flow control member 110 is allowed to deflate, allowing oxygenated blood to flow from the heart to the arch vessels, the descending aorta, and to the coronary arteries. The heart should then spontaneously resume normal sinus rhythm, however, if necessary, cardioversion or defibrillation shocks may be applied to restart the heart. The patient is then weaned off the bypass and the aortic catheter, and other cannulas, are withdrawn. The alternate embodiment configured for antegrade deployment would be used similarly, except that access to the patient's circulatory system would be made through a central access by an aortotomy or incision directly into the ascending aorta.

Modification of the operational characteristics or procedures set forth above for use in vessels other than the aorta for perfusion of blood to branch vessels are readily ascertainable by those skilled in the art in view of the present disclosure.

Figure 6:
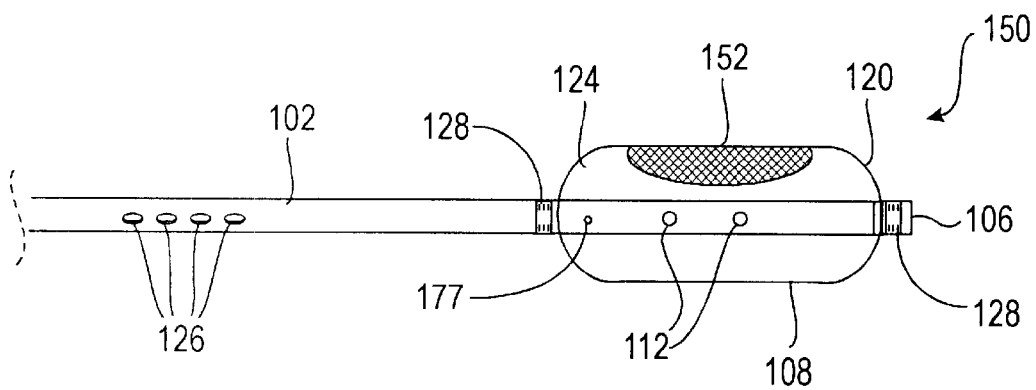
FIG. 6 is a side view of a shaft portion of a second embodiment of an expanded or deployed single-balloon flow control member with a porous window.
Figure 7:
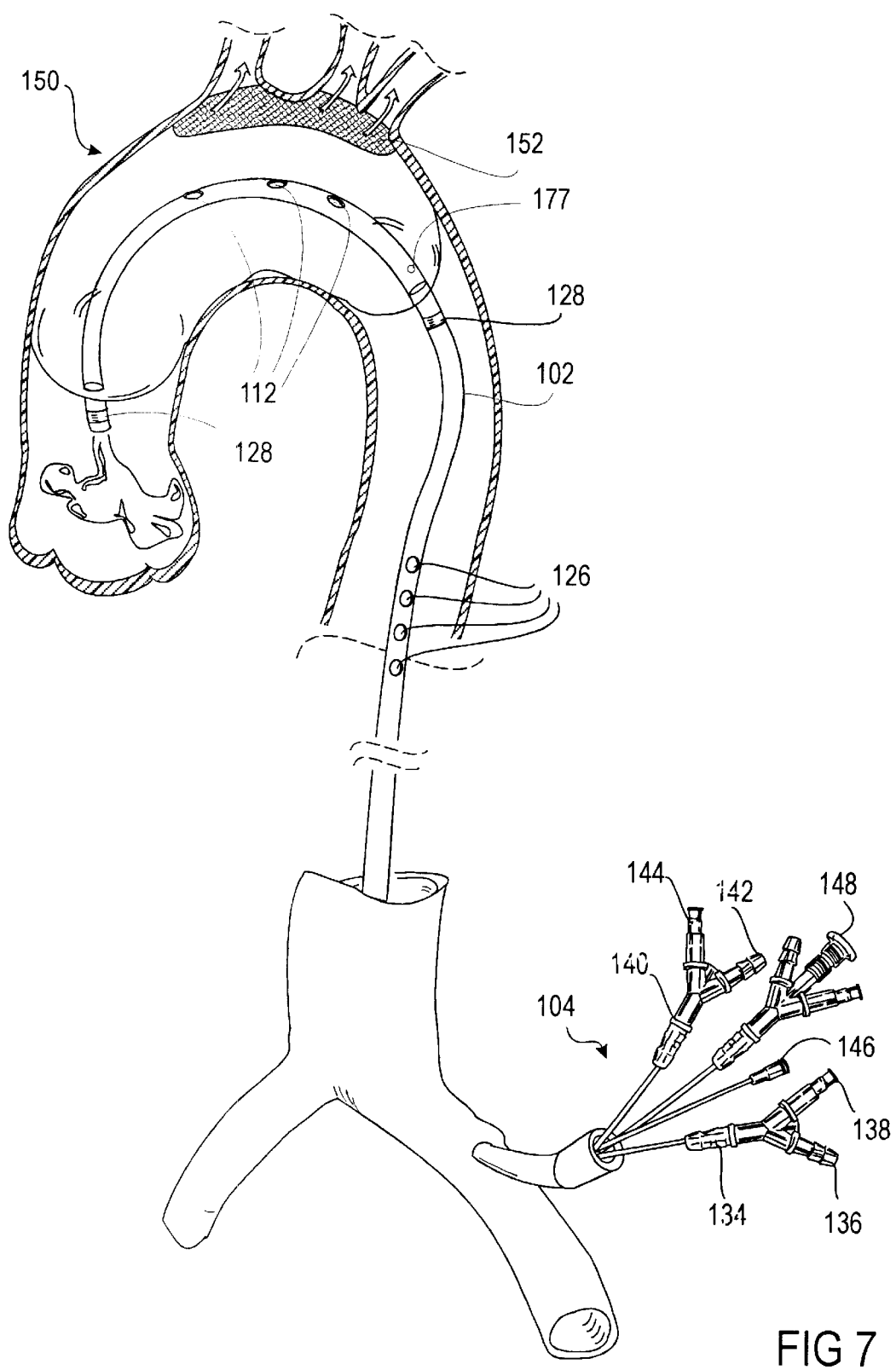
FIG. 7 is a side view of the aortic catheter of FIG. 6 deployed or expanded in the aorta of a patient, showing the porous window aligned with the ostia of the arch vessels.

In an alternate embodiment seen in FIGS. 6 and 7, the flow control member 150 comprises a nonporous balloon with a porous window 152. In this variation, the catheter 100 may be made of the same materials as those described in relation to the catheter 100 of FIGS. 1 through 5. Common numbers refer to common assembly components, therefore the description of these parts as explained in connection with FIGS. 1 through 4 is incorporated by reference into this illustrative embodiment and all others to follow. The relative position, size and shape of the porous window 152 is provided only as an example and any size shape or configuration may be implemented. In this example, the porous window 152 is positioned approximately symmetrically with respect to the balloon-shaped flow control member 150. FIG. 7 shows the aortic catheter of FIG. 6 deployed within a patient's aorta illustrating the relative position of the porous window 152 relative to the ostia of the arch vessels. In this example, the porous window 152 is positioned asymmetrically with respect to the balloon-shaped flow control member 150 to accommodate a variation in the geometry of a patient's aortic arch.

Figure 8:
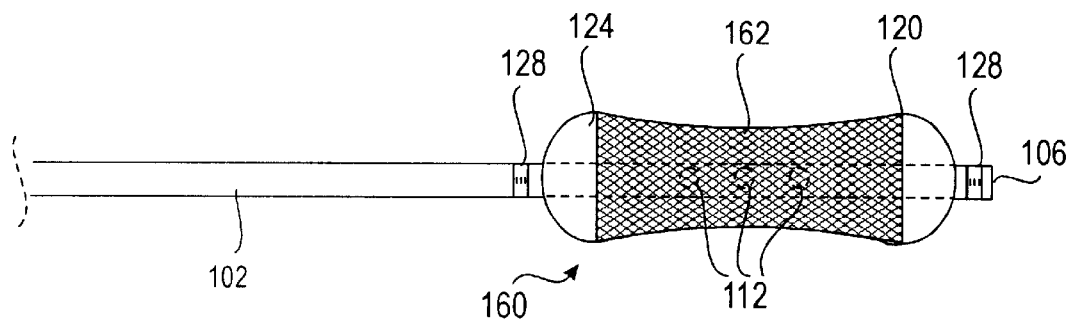
FIG. 8 is a side view of a third alternate embodiment of the primary flow control member of the present invention wherein the porous middle portion of the primary flow control member has a deployed diameter less than the deployed diameter of the proximal and distal ends.

In an alternate embodiment shown in FIG. 8, the flow control member 160 includes a porous middle portion 162 with an inflated or deployed diameter less than the diameter of the aortic lumen when the proximal 124 and distal 120 ends are expanded and occluding the aorta. In the embodiments wherein the middle porous section contacts the aortic lumen the effective perfusion area may be limited to the area at the openings of the ostia since the rest of the porous portion will be effectively occluded by the aortic wall. The advantage of the configuration associated with FIG. 8 is that the middle porous section 162 avoids substantial contact with the aortic wall allowing a greater effective filter and perfusion surface area to the arch vessels since perfusion is free to pass through all the mesh material and into the arch vessels. This enables a finer mesh to be used since the effective filter and perfusion surface area is not limited to the openings of the arch vessels.

The occlusion member 160 of FIG. 8 may be made of different materials which will enable the proximal and distal ends to be more easily inflatable or expandable than the middle porous portion 162 which has the resultant effect of differing outer diameter proportions. For example, the proximal 124 and distal 120 ends may be made of a flexible elastomer such as silicone or latex and the middle portion may be made of a less flexible polyurethane or nylon. Alternatively, another way to achieve the larger ends and a narrower middle portion is to use mechanical supports, external clamps, external heat shrink or the like on the middle portion to essentially restrict the middle portion relative to the ends. In addition, a single material can be used and the desired shape can be achieved by varying the wall thickness of the occlusion member 160. For example, dipping, molding or extruding the occlusion member are all methods, which may be utilized for creating an occlusion member having a varying wall thickness. Furthermore, the ends of the occlusion member 160 may be fatigued through the manufacturing process to create a thinner or more flexible material.

Figure 9:
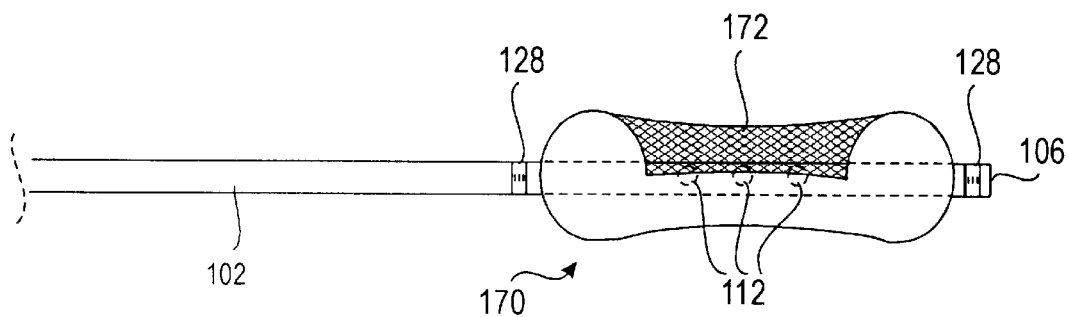
FIG. 9 is a side view of an alternate embodiment of the primary flow control member of the invention with a porous window, where the middle portion of the flow control member has a deployed diameter less than the deployed diameter of the proximal and distal ends of the flow control member.

The embodiment seen in FIG. 9 discloses a flow control member 170 comprising a nonporous balloon with a porous window 172. The relative position, size and shape of the porous window 172 is provided only as an example, and in other embodiments the porous window 172 may be any desirable position, size or shape. The catheter of FIG. 9 is otherwise similar to the catheter of FIG. 8 as previously described, and the same benefit of increased filter surface area may be obtained. In this embodiment, the smaller diameter of the middle portion also reduces the criticality of positioning the window 172 over the ostia of the arch vessels.

Figure 10:
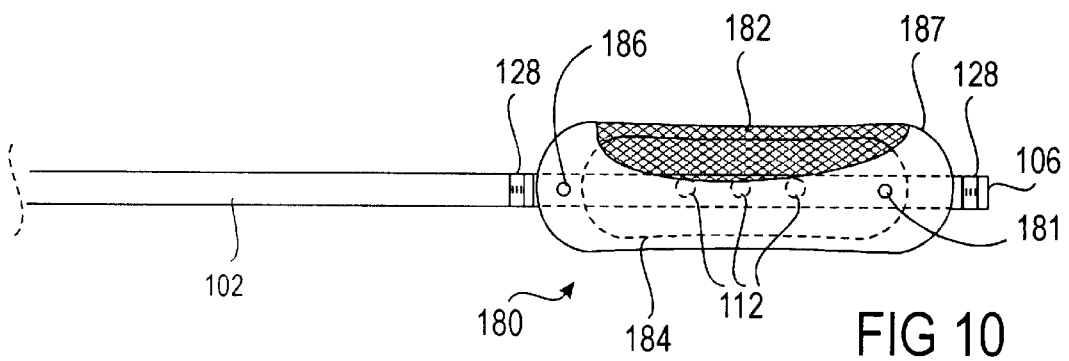
FIG. 10 is a side view of an embodiment where the flow control member of the invention comprises an inner balloon and an outer balloon.
Figure 11:
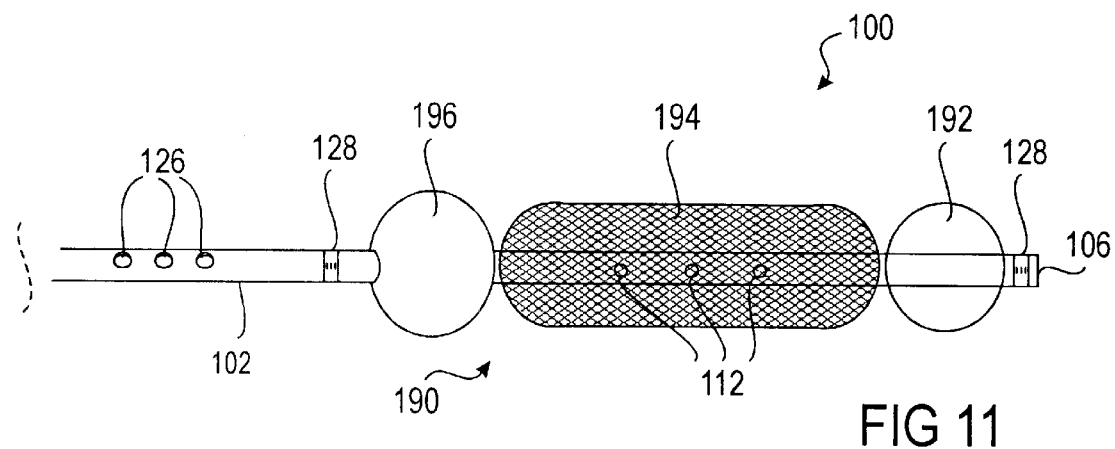
FIG. 11 is a side view of an embodiment of the primary flow control member wherein the primary flow control member is a compound structure comprised of three flow control elements.

In another embodiment, seen in FIG. 10, a flow control member 180 comprises a first outer flow control element or outer balloon 187 and a second inner flow control element or inner balloon 184 positioned within the first outer balloon 187. The first outer balloon 182 comprises a porous material or includes one or more porous sections 182. The second inner balloon 184 is preferably nonporous. When the second inner balloon 184 is fully inflated, the outer surface of the second inner balloon 184 contacts the inner surface of the first outer balloon 187 preventing escape of perfused fluid through the porous sections of the first outer balloon 187. When the first inner balloon 187 is fully or partially deflated, perfusion is allowed to resume through outer balloon 187. In this embodiment, separate lumens connecting to the outer balloon port 186 and the inner balloon port 181 are required for inflating and deflating the first outer balloon 182 and the second inner balloon 184 independently of each other.

In embodiments seen in FIGS. 11 through 17, the catheter 100 is shown and will be described having a flow control member comprising a plurality of flow control elements. For example, FIG. 11 discloses a flow control member 190 comprising a set of three adjacent flow control elements. In this embodiment, the flow control elements include a first balloon 192, a second balloon 194, and a third balloon 196. In alternate embodiments, any desirable or practical valves, may be substituted for balloons 192 and 196.

The first balloon 192, located nearest the distal end 106 of the aortic catheter 100, is preferably comprised of a nonporous material, and is intended to occlude the ascending aorta between the coronary arteries and the arch vessels, and to prevent fluid perfused through the second porous balloon 194 from entering the ascending aorta in a retrograde direction. The second porous balloon 194 is positioned adjacent the proximal side of the first balloon 192. The second balloon 194 is preferably formed of a porous material, includes porous sections, or includes other means for allowing a controlled flow rate of perfused fluid to pass through. The third balloon 196 is located adjacent the second balloon 194 and is preferably comprised of a nonporous material. In variations where the aortic catheter 100 is to be introduced directly into the ascending aorta the balloon position is reversed relative to the aorta such that the first occlusion balloon 192 resides in the descending aorta and the third occlusion balloon 196 resides in the ascending aorta. The purpose of the third balloon 196 is primarily for occluding the aorta to prevent fluid perfused through the porous second balloon 194 from entering the descending aorta. The porous second balloon 194 may be configured with a deployed diameter equal to or greater than the aortic lumen in order to contact the aortic wall after inflation, or it may be configured with a deployed diameter smaller than the aortic lumen so that, after inflation, it is not in substantial contact with the aortic lumen. The advantage of configuring the second porous balloon 194 to contact the aortic wall is that the force or friction generated by contact with the aortic wall may resist migration of the flow control member 190. The advantage of configuring the porous second balloon to avoid substantial contact with the aortic wall is that a greater effective filter surface area is achieved because perfusion may not be limited to passing through the mesh material over the arch vessels, consequently, a finer mesh may be used while still achieving a desired flow rate at a desired pressure.

Figure 12:
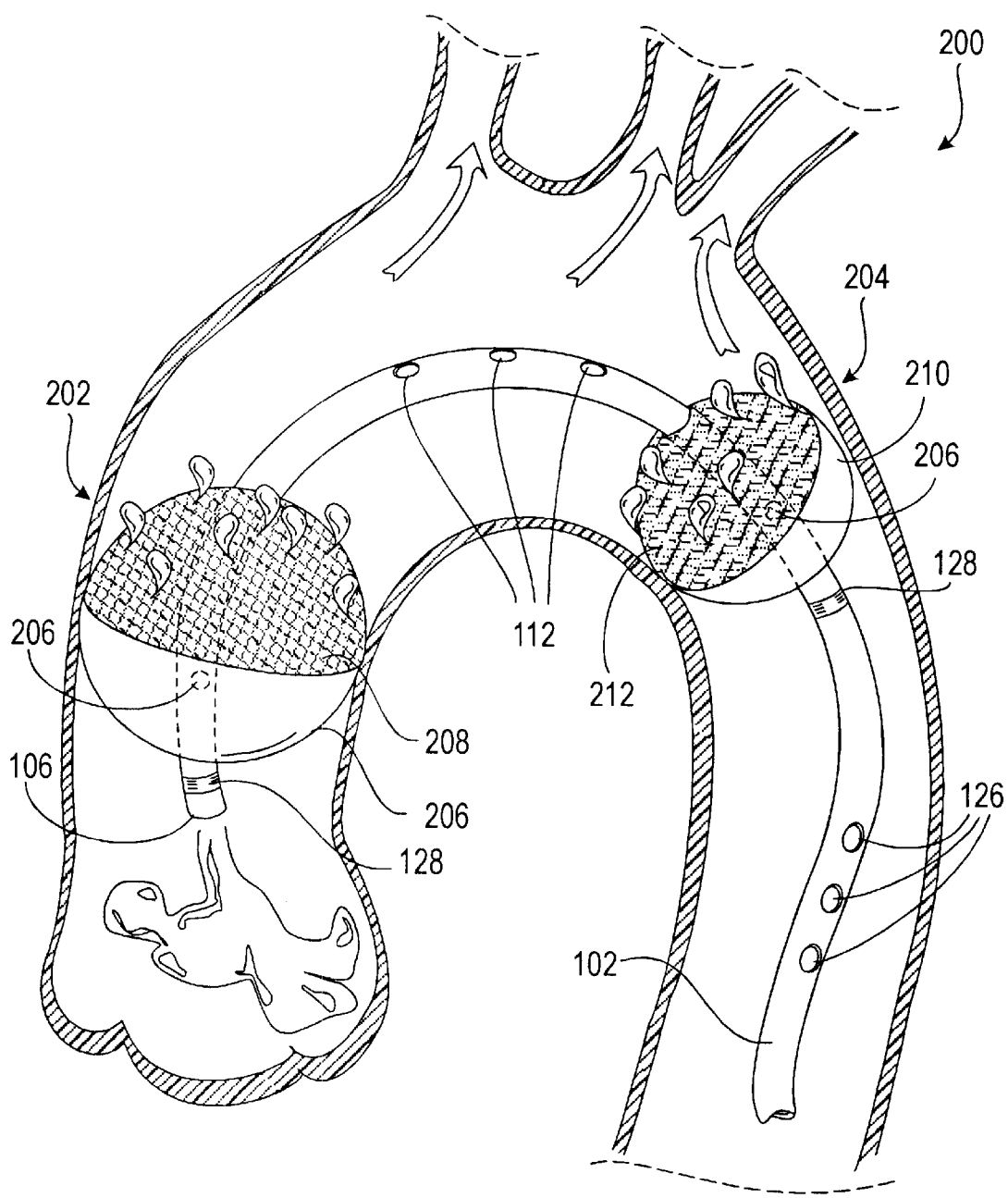
FIG. 12 is a side view of another embodiment of the primary flow control member wherein the primary flow control member is a compound structure comprised of two flow control elements deployed in a patients aorta.

Another embodiment of the distal flow control member is seen in FIG. 12, which discloses a flow control member 200 comprising two flow control elements 202 and 204 spaced apart so that, in use, one flow control element is positioned on each side of the arch vessels. In the embodiment shown, the flow control elements 202 and 204 comprise inflatable balloons. The first flow control element 202, located nearest the distal end of the aortic catheter 200, preferably comprises a nonporous section 206 on the distal side of the flow control element 202, and a porous section 208 located on the proximal side of the flow control element 202. The second flow control element 204 preferably comprises a nonporous section 210 located on the proximal side of the flow control element 204, and a porous section 212 located on the distal side of the flow control element 204. The deployment/perfusion ports 206 are located in the first and second flow control elements 202 and 204. The same or separate inflation/perfusion lumens may be used for flow control elements 202 and 204. In an alternate embodiment, only one of the balloons 202 or 204 may include a porous section. Alternatively, the first flow control element 202 and second flow control element 204 may be reversed in orientation such that the non-permeable portions are reversed with respect to the permeable portions. In this position, cardioplegia may be delivered to the aortic root through permeable portion 208 while blood is delivered to the corporeal body through permeable portion 212 and the arch receives blood through arch perfusion ports 112 at a flow sufficient to maintain the viability of the brain.

Figure 13:
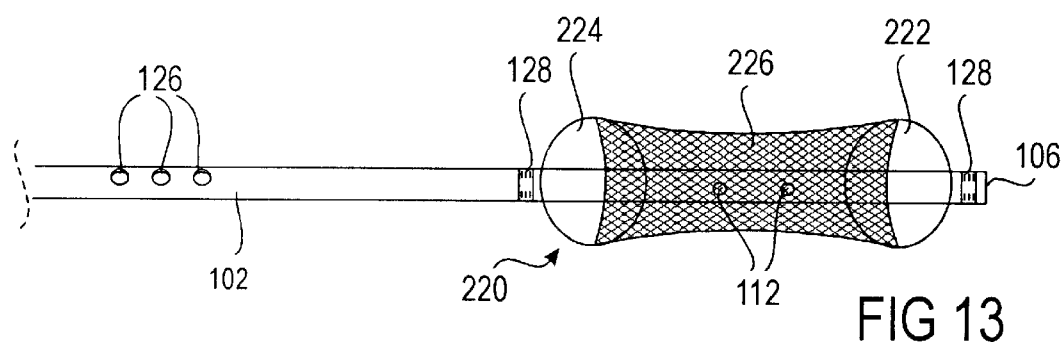
FIG. 13 is a side view of an embodiment of the primary flow control member wherein the primary flow control member is a compound structure comprised of three flow control elements with a filter mesh coupled to and deployed between them.
Figure 14:
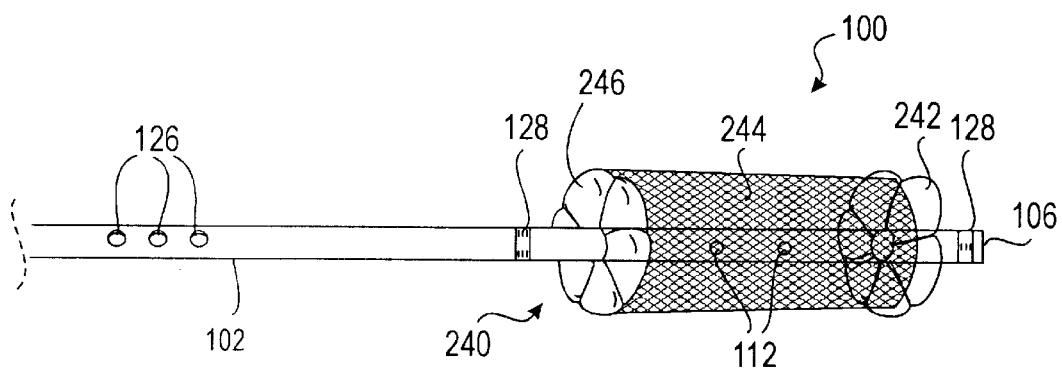
FIG. 14 is a side view of another embodiment of the primary flow control member wherein the primary flow control member is a compound structure comprised of two valve flow control elements and one porous inflatable balloon flow control member.

FIG. 13 discloses a flow control member 220 comprising two flow control elements 222 and 224 spaced apart, as in the previous embodiment, so that, in use, one flow control element is positioned on each side of the arch vessels. However in this embodiment, a mesh or porous filter 226 is coupled between the balloons. In this embodiment, the first and second flow control elements 222 and 224 are nonporous balloons. The balloons may be deployed by using a single deployment/perfusion lumen, or in alternate embodiments, a separate lumen may be used to deploy the flow control elements 222 and 224 independently.

In alternate embodiments, valves of various varieties, such as those described in U.S. Pat. Nos. 5,833,671, 5,827,237 by John A. Macoviak and Michael Ross; and U.S. patent application Ser. No. 08/665,635, filed Jun. 17, 1996, by John A. Macoviak and Michael Ross which have previously been incorporated by reference may be used instead of one or more of the inflatable balloons of the flow control elements previously described. For example, FIG. 14 discloses a primary flow control member 240 similar to that disclosed in FIG. 12, comprising a first flow control element 242, a second flow control element or inflatable balloon 244, and a third flow control element 246. However, in this embodiment, flow control elements 242 and 246 are valves. Any desirable or practical valves, such as those described in U.S. Pat. Nos. 5,833,671, 5,827,237 by John A. Macoviak and Michael Ross; and U.S. patent application Ser. No. 08/665,635, filed Jun. 17, 1996, by John A. Macoviak and Michael Ross, may be substituted for balloons 192 and 196 which have been described in the previous embodiments. Flow control element 244 is an inflatable balloon comprising a porous material or having porous sections or the like.

The first flow control element 242 is located nearest the distal end 106 of the aortic catheter 100, and is intended to occlude the ascending aorta between the coronary arteries and the arch vessels when introduced in the retrograde direction by way of femoral access and is sized and configured to prevent fluid perfused through the balloon 244 from entering the ascending aorta in a retrograde direction. The third flow control element 246 is positioned adjacent the distal side of the balloon 244. The purpose of the third flow control element 246 is primarily for occluding the aorta to prevent fluid perfused through the second porous balloon from entering the descending aorta and to isolate cardioplegia. The balloon 244 may be configured with a deployed diameter equal to or greater than the aortic lumen in order to contact the aortic wall after inflation, or it may be configured with a deployed circumference smaller than the aortic lumen so that, in use, it is not in substantial contact with the aortic lumen. The advantage of configuring the balloon 244 to contact the aortic wall is that the force or friction generated by contact with the aortic wall may resist migration of the flow control member 240 or cannula 100. The advantage in configuring the balloon 244 to avoid substantial contact with the aortic wall is that a greater effective filter surface area is achieved because perfusion is not limited to passing through the mesh material of the balloon 244 over the arch vessels. Consequently, a finer mesh may be used. Preferably the catheter shaft 102 includes one or more lumens for deployment of the flow control elements 242 and 246 separate from the inflation/perfusion lumen for balloon 244.

Figure 15:
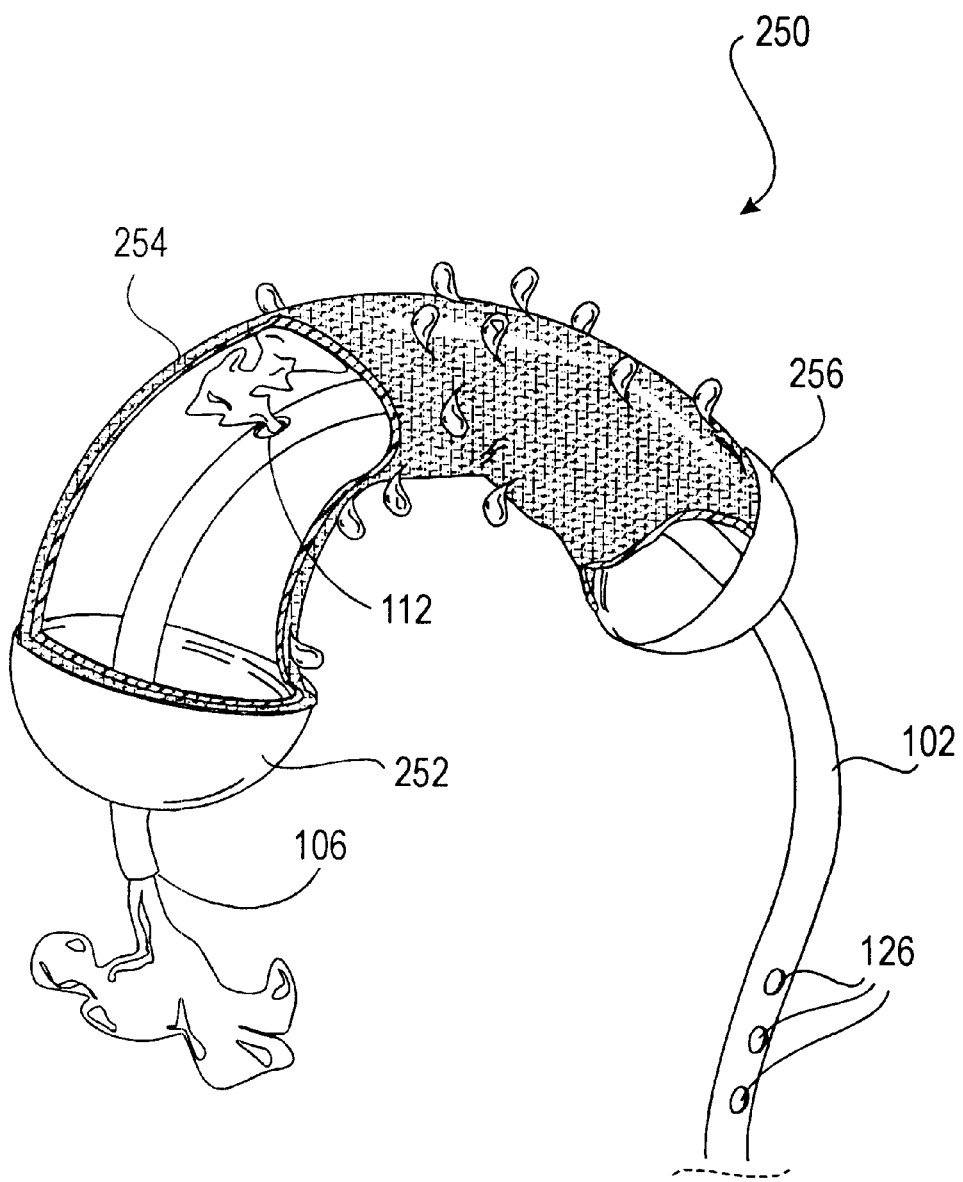
FIG. 15 is a side view of another embodiment of the primary flow control member wherein the primary flow control member is a compound structure comprised of two end cap valve flow control elements and one porous inflatable balloon flow control element partially received within each valve element.
Figure 16:
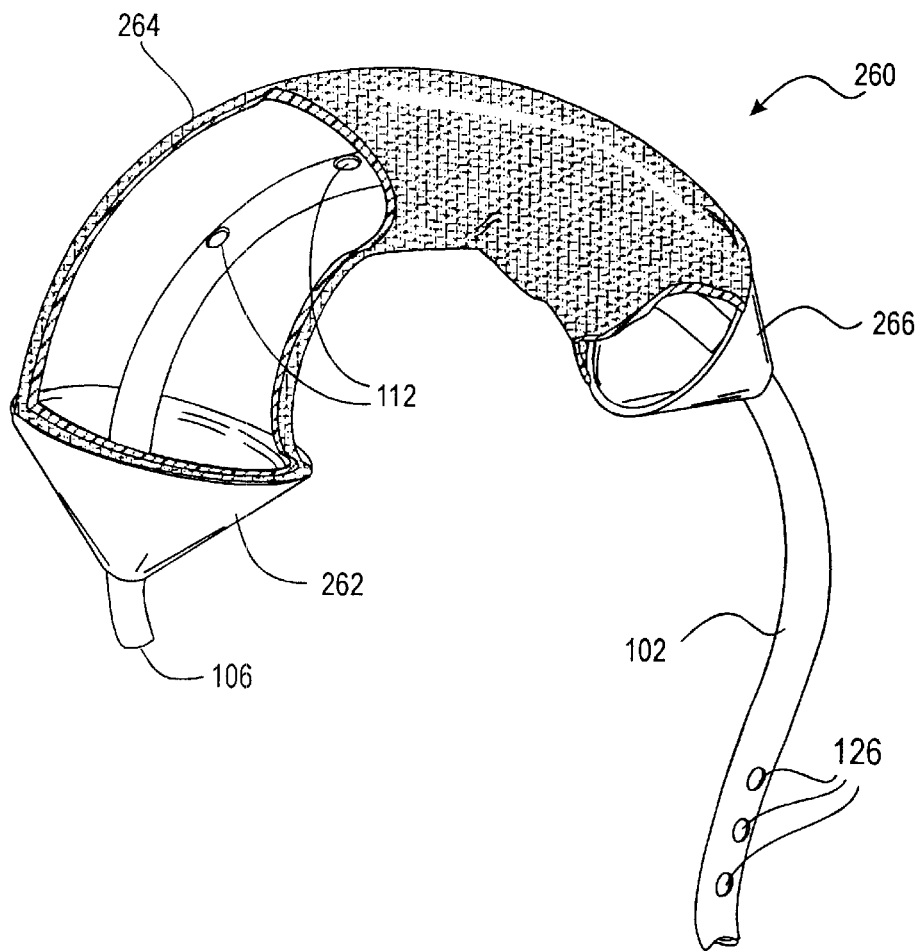
FIG. 16 is a side view of an embodiment of the primary flow control member similar to that shown in FIG. 15, except the valve elements are conical.

In the embodiment shown in FIG. 15, the flow control member 250 is shown with valves 252 and 256 being end cap valves that are deployed by inflation or deployment of the second flow control element 254. Consequently, the end cap valves 252 and 256 do not require separate deployment lumens, as deployment of the inflatable middle flow control element 254 will deploy them. The end cap valves may be any desired shape or configuration. For example, FIG. 16 shows a flow control member 260 similar to that disclosed in FIG. 15, but with conical end cap valves 262 and 266. The end cap valves may be made of any suitable materials such polyurethanes, polyethylene terephthalate (PET), polyvinyl chloride (PVC), polyolefin, latex and ethylene vinyl acetate (EVA).

Figure 17:
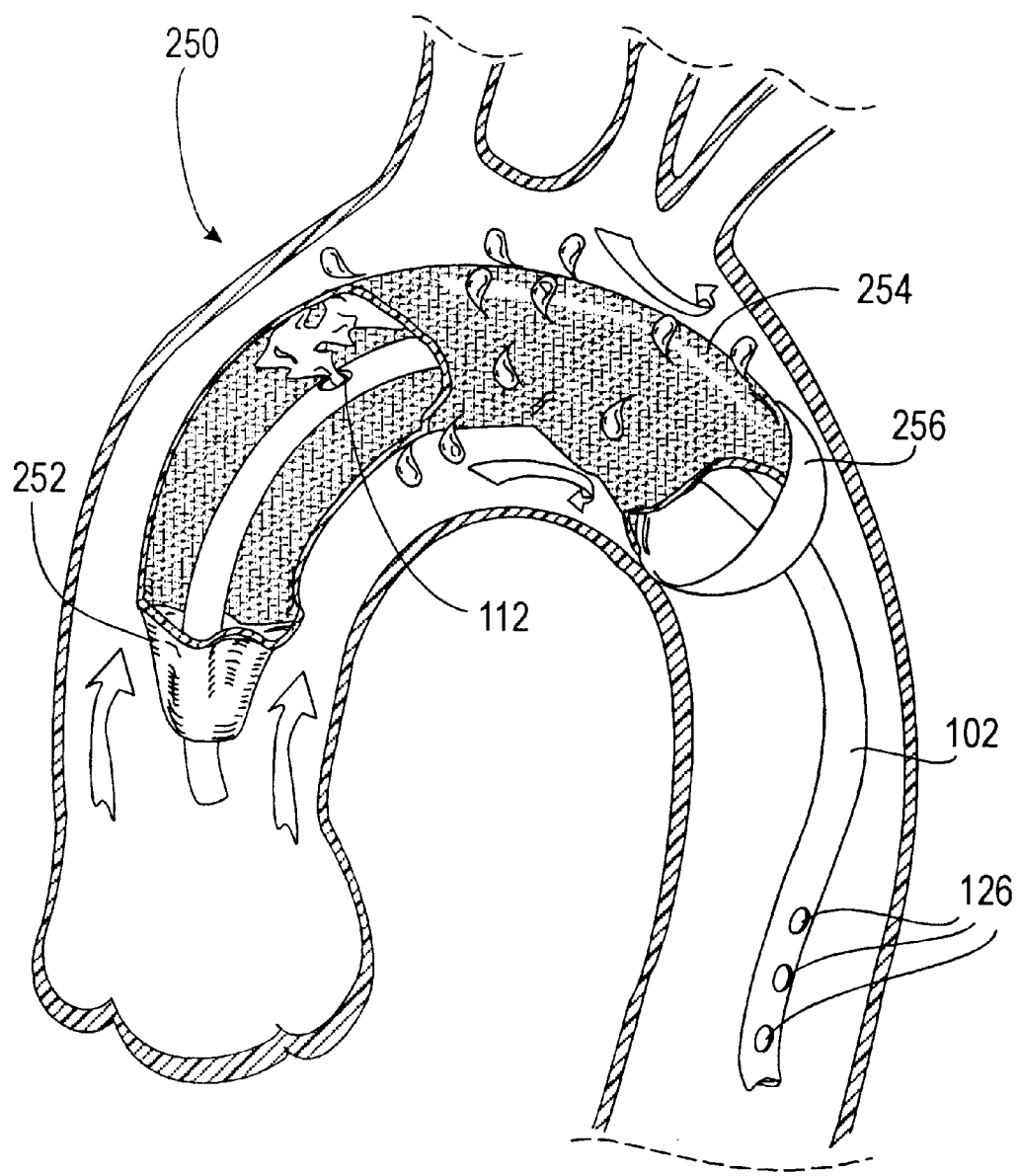
FIG. 17 is a side view of the embodiment of the primary flow control member similar to that shown in FIG. 15 deployed within a patient's aortic arch, and showing the distal valve element partially collapsed.

FIG. 17 shows the embodiment of the catheter of FIG. 15 deployed in an aorta with the first flow control element 252 shown in a semi-collapsed condition. It may be an advantage to wean a patient off cardiopulmonary bypass slowly, after the completion of a procedure, by providing a means for transitioning between complete occlusion of the aorta and perfusion by cardiopulmonary bypass and normal heart function. Reducing the pressure in the second flow control member reduces the support of the flow control members 252 and 256. Fluid pressure generated by contraction of the ventricle temporarily partially collapses the flow control element 252. Thus, by adjusting the pressure in the second flow control element 254 downward, a controlled flow of blood from the heart is allowed to enter the arch vessels and/or the descending aorta.

Figure 18:
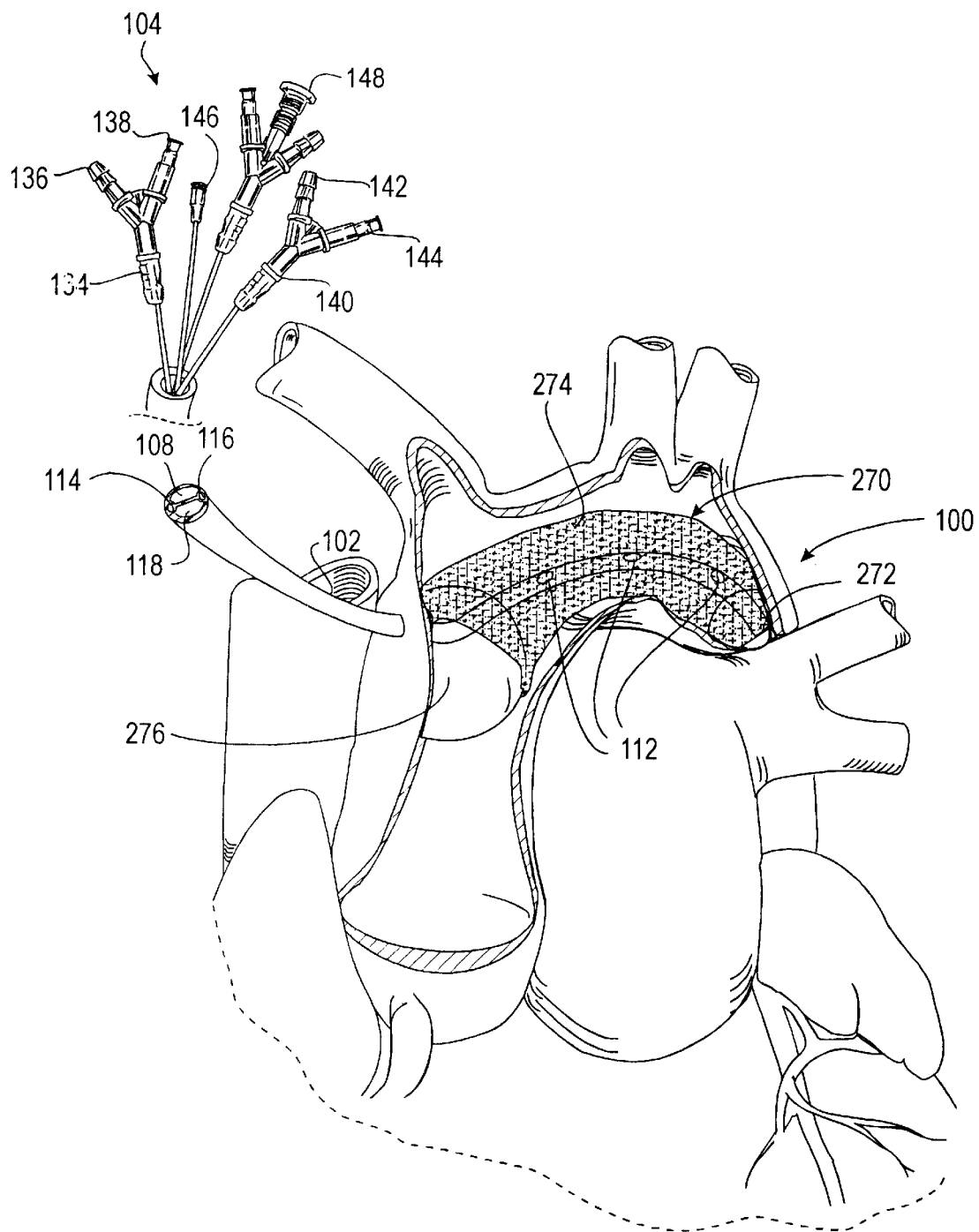
FIG. 18 is a side view of an embodiment of the primary flow control member of the invention configured for antegrade deployment.

The previous embodiments have been described using a catheter configured for a retrograde approach to the aorta from a peripheral vessel such as the femoral artery. Each of the described embodiments of the invention could easily be modified for alternate deployment means. For example, FIG. 18 shows a catheter 100 configured for central antegrade deployment in the aortic arch through an aortotomy or direct puncture in the ascending aorta. The catheter 100 and flow control member 270 is configured similarly to that disclosed in FIG. 3, comprising an inflatable balloon with nonporous sections 272 and 276, and a porous middle portion 274. In this embodiment, the guidewire lumen 116 may be used for corporeal perfusion after the guidewire is removed or alternatively a separate catheter may be inserted either into the femoral artery or the subclavian to perfuse the corporeal circulation, or alternatively corporeal perfusion can be provided through a corporeal lumen 118 and downstream corporeal port 126 distal to the flow control member 270. Other embodiments of the invention may be configured for peripheral insertion through the subclavian, femoral or auxiliary arteries, as can be seen in U.S. patent application Ser. No. 09/205,753.

Figure 19:
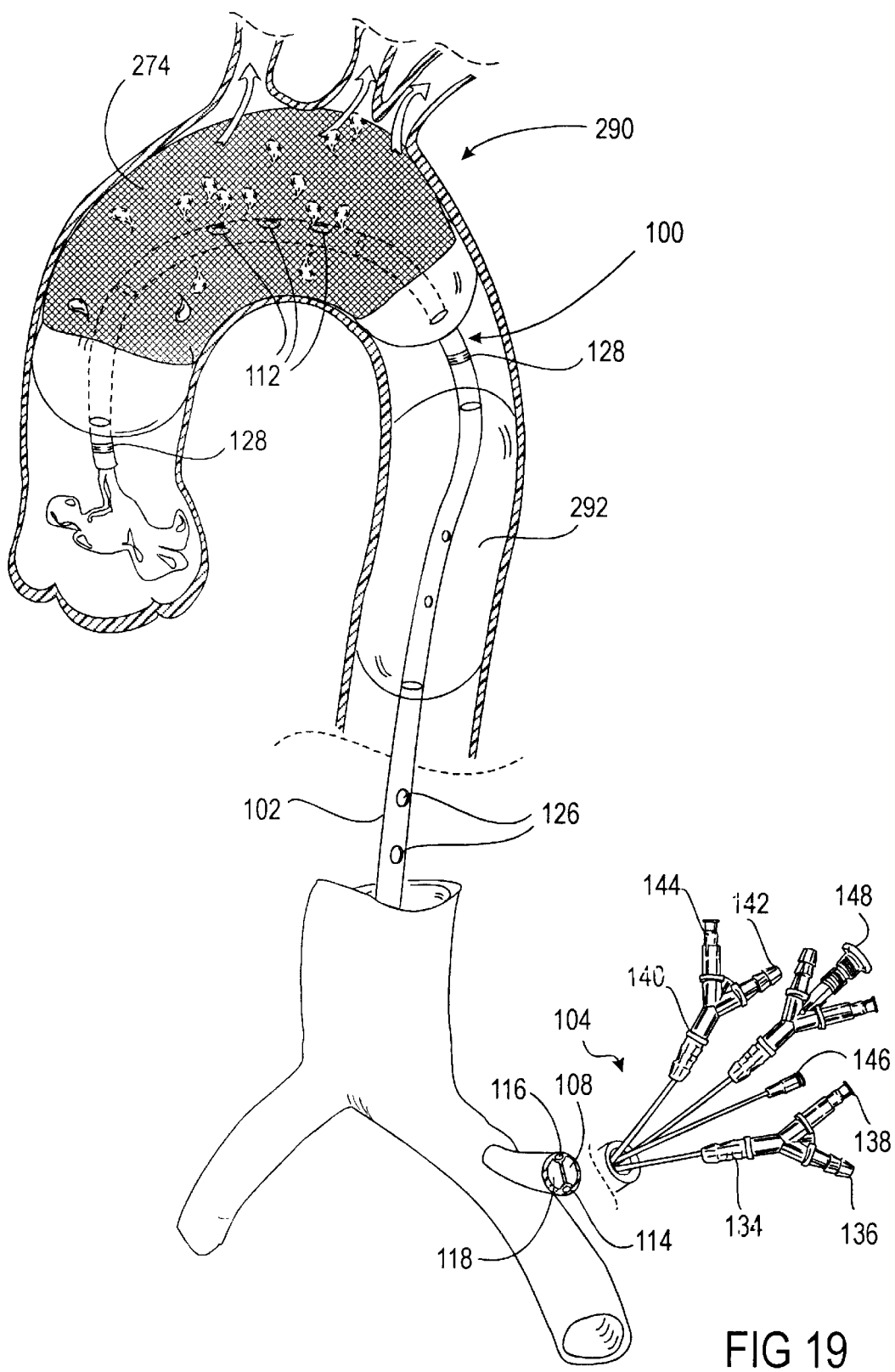
FIG. 19 is a side view of an embodiment the catheter of the invention further comprising an auxiliary flow control member positioned in the patient's descending aorta.

Any embodiments of the catheter of the invention described above may further include auxiliary flow control members. The auxiliary flow control members may be used to further compartmentalize the patient's circulatory system, or may be used for other functions such as assisting in securely anchoring the catheter in a chosen position. Accordingly, the auxiliary flow control members may be inflatable balloons, deployable valves, or combinations thereof. An example of an auxiliary flow control member is seen in FIG. 19. The catheter of FIG. 19 is configured similarly to the catheter disclosed in FIG. 4, except that the catheter of FIG. 19 comprises an additional or auxiliary flow control member 292 coupled to the catheter shaft 102 proximate, but spaced apart from, the primary flow control member 290. The auxiliary flow control member 292 is mounted to the distal portion of the catheter shaft 102 proximal to, but spaced apart from, the primary flow control member 290. The distance between the primary flow control member 290 and the auxiliary flow control member 292 is between approximately 0.5 cm and 10 cm, and is chosen so that when the aortic catheter 100 is deployed with the primary flow control member 290 over the ostia of the arch vessels, the auxiliary flow control member 292 will be positioned in the descending aorta. Use of an auxiliary flow control member 292 to anchor the catheter 100 may allow the use of a lower inflation pressure in the porous balloon as it is no longer depended on for preventing migration of the catheter 100. This may avoid possible damage to the aorta, which may result from the use of higher pressures to prevent migration.

The auxiliary flow control member 292 is shown in this embodiment in the form of an expandable inflatable balloon bonded to the catheter shaft 202 by heat welding or with an adhesive. The auxiliary flow control member 292 preferably has a length that is longer than the length of the primary flow control member 290, or alternatively may be shorter so long as the function of anchoring the catheter 100 is accomplished. Suitable materials for the inflatable anchor member 292 include, but are not limited to, elastomers, thermoplastic elastomers, polyvinylchloride, polyurethane, polyethylene, polyamides, polyesters, silicone, latex, and alloys or copolymers and reinforced composites thereof. In addition, the outer surface of the anchor member 292 may include a friction increasing means such as a friction increasing coating or texture to increase friction between the anchor member 292 and the aortic wall when deployed. In the embodiment shown, the corporeal perfusion ports 126 are located on the catheter shaft 102 proximate the anchoring member.

FIG. 19 illustrates the aortic catheter 100 of the present invention deployed in the aorta illustrating the functional features and material attributes of the flow control member 290 in use. The flow control member 290 is positioned within the aortic arch with the porous middle portion 274 covering the ostia of the arch vessels. A selected fluid, such as oxygenated normothermic blood, oxygenated hypothermic blood, blood substitutes such as PERFLUBRON or other perfluorocarbon compounds, radiopaque dyes for angiography, or the like, is introduced through the flow control member inflation and perfusion lumen 108 into the inflatable flow control member 290. Some selected fluid may seep out through the porous middle portion 274 during inflation, but at a rate less than the rate at which the selected fluid enters the flow control member 290. In an alternate embodiment, it may be preferable to initially inflate the flow control member 290 with a more viscous solution, for example a radiopaque contrast agent mixed with saline, that will flow through the porous middle portion 274 at a rate slower than the selected perfusion fluid will leak.

When the correct pressure is attained, the flow control member 290 occludes blood flow through the aortic lumen. The selected fluid used to inflate the flow control member 290 may escape through the porous portion 274 at a known rate into the arch vessels. The flow rate may be adjustable by adjusting the pressure within the flow control member 290. Contact with the aortic wall and the middle porous portion 274 of the flow control member 290 will reduce or prevent seepage of the selected fluid through sections of the porous middle portion 274 of the flow control member 290 not aligned with the arch vessels. The middle porous portion 274 of the flow control member 290 contacting the aortic wall may also provided resistance to the migration of the flow control member 290 or cannula 100.

Preferably, the aortic catheter 100 includes one or more location markers 128, such as radiopaque markers and/or sonoreflective markers, to enhance imaging of the aortic catheter 100 during deployment using standard fluoroscopy, ultrasound, MRI, MRA, transesophageal echocardiography, or other techniques. A radiopaque location marker 128 may be formed as a ring or disk of dense radiopaque metal such as gold, platinum, tantalum, tungsten, or compounds or alloys thereof, or a ring of a polymer or adhesive material heavily loaded with a radiopaque filler material.

In use, the catheter 100 is advanced up the descending aorta and across the aortic arch, under fluoroscopic or ultrasound guidance with the aid of a guidewire within the guidewire lumen 116. The aortic catheter 100 is advanced until the primary flow control member 290 is positioned in the aortic arch. This may be determined by reference to the radiopaque marker or markers 128. Using a multihead cardiopulmonary bypass pump or the like, perfusion of oxygenated blood is started through perfusion lumen 108 and out the perfusion ports 112. The flow control member 290 is then inflated to occlude the aortic arch using a selected perfusion fluid such as oxygenated blood. When the correct pressure is achieved, the perfusion fluid flows from the flow control member 290 and enters the arch vessels. The rate of flow of the perfusion fluid may be controlled by adjusting the pressure within the flow control member 290. At the completion of the surgical procedure, auxiliary member 292 is deflated and thereafter the flow control member 290 is allowed to deflate, allowing oxygenated blood to flow from the heart to the arch vessels, the descending aorta, and to the coronary arteries. The heart should then spontaneously resume normal sinus rhythm, however, if necessary, cardioversion or defibrillation shocks may be applied to restart the heart. The patient is then weaned off the bypass and the aortic catheter, and other cannulas, are withdrawn. The alternate embodiment configured for antegrade deployment would be used similarly, except that access to the patient's circulatory system would be made through a central access by an aortotomy or incision directly into the ascending aorta.

In use, the aortic catheter 100 of any of the embodiments described above is introduced into the patient's circulatory system through a peripheral artery such as the femoral artery, by the percutaneous Seldinger technique, through an introducer sheath, via an arterial cutdown or centrally by means of a median sternotomy or mini-thorocotmy.

Modification of the operational characteristics or procedures set forth above for use in vessels other than the aorta for perfusion of blood to branch vessels are readily ascertainable by those skilled in the art in view of the present disclosure.

What is claimed is:

1. A catheter for perfusing a branch lumen connected to a first body lumen in a patient comprising:
    an elongated catheter shaft configured for introduction into the first body lumen of the patient, said catheter shaft having a proximal end and a distal end; and
    a flow control member coupled to said elongated catheter shaft having an expanded diameter sufficient to block blood flow through the first body lumen when deployed, said flow control member comprising a distal impermeable portion, a middle portion, and a proximal impermeable portion, said middle portion comprising a porous section, whereby a fluid used to inflate said middle portion perfuses through said porous section, perfuse the branch lumen;
    wherein said porous section is configured as a window of porous material positioned on one side of said middle portion; and
    further comprising at least one auxiliary flow control member coupled to said elongated catheter shaft distal to said flow control member.

2. A catheter for perfusing a branch lumen connected to a first body lumen in a patient comprising:
    an elongated catheter shaft configured for introduction into the first body lumen of the patient, said catheter shaft having a proximal end and a distal end; and
    a flow control member coupled to said elongated catheter shaft having an expanded diameter sufficient to block blood flow through the first body lumen when deployed, said flow control member comprising a distal impermeable portion, a middle portion, and a proximal impermeable portion, said middle portion comprising a porous section, whereby a fluid used to inflate said middle portion perfuses through said porous section, to perfuse the branch lumen;
    wherein said porous section is configured as a window of porous material positioned on one side of said middle portion; and
    further comprising at least one auxiliary flow control member coupled to said elongated catheter shaft proximal to said flow control member.

3. A catheter for perfusing a branch lumen connected to a first body lumen in a patient comprising:
    an elongated catheter shaft configured for introduction into the first body lumen of the patient, said catheter shaft having a proximal end and a distal end; and
    a flow control member coupled to said elongated catheter shaft having an expanded diameter sufficient to block blood flow through the first body lumen when deployed, said flow control member comprising a distal impermeable portion, a middle portion, and a proximal impermeable portion, said middle portion comprising a porous section, whereby a fluid used to inflate said middle portion perfuses through said porous section, to perfuse the branch lumen;
    wherein said porous section is configured as a window of porous material positioned on one side of said middle portion; and
    wherein said porous section is configured as a plurality of windows of porous material.

4. A catheter for perfusing a branch lumen connected to an aortic arch lumen in a patient comprising:
    a catheter shaft having a distal end configured to be inserted into a first body lumen of the patient and navigated into the patient's aortic arch lumen and a proximal portion extending outside the first body lumen of the patient when said distal end is in an operative position and wherein said proximal portion is in fluid communication with an external perfusion pump and is configured to provide blood flow to the patient's cerebral circulation through at least one perfusion port in an exterior of said catheter shaft and at a flow rate sufficient to maintain viability of the patient's brain;
    a flow control member positioned proximate the distal end of the catheter shaft configured for expanding from said catheter shaft to at least partially occlude the aortic arch lumen, wherein said flow control member has a distal impermeable portion, a middle portion, and a proximal impermeable portion, said middle portion comprising a porous portion, said porous portion having permeable portions of sufficient size to allow fluid to flow therethrough to the patient's arch vessels and said at least one occlusive end is sized and dimensioned such that when placed in the operative position upstream of the patient's brachiocephalic artery said occlusive end is capable of expanding radially to a diameter at least the size of an inside diameter of the patient's aortic arch lumen; and a corporeal perfusion lumen having a distal end configured to reside inside the lumen of the patient's aorta when placed in an operative position and a proximal portion extending outside the first body lumen of the patient and configured for being coupled to said external perfusion pump and of sufficient size and internal diameter to communicate fluid from said external perfusion pump to a corporeal perfusion port proximate said external end to sustain metabolic demands of the patient's body.

5. The aortic catheter of claim 4, wherein said porous portion comprises one or more porous windows.

6. The catheter of claim 4, wherein said porous portion has a deployed diameter less than the deployed diameter of said occlusive end.

7. The catheter of claim 4, wherein a known rate of perfusion can be established by adjusting the pressure within the flow control member.

8. The catheter of claim 4, further comprising at least one auxiliary flow control member coupled to said elongated catheter distal to said flow control member.

9. The catheter of claim 4, further comprising at least one auxiliary flow control member coupled to said elongated catheter proximal to said flow control member.

10. The catheter of claim 4, wherein said porous portion comprises a filter.

11. The catheter of claim 4, wherein said porous portion is comprised of a filter material.

12. The catheter of claim 5, wherein said one or more porous windows comprise a filter.

13. A catheter for perfusing a branch lumen connected to an aortic arch lumen in a patient comprising:

a catheter shaft having a distal end, a proximal portion and a flow control member positioned between said proximal portion and said distal end, said flow control member having a distal impermeable portion, a middle portion, and a proximal impermeable portion, said middle portion comprising a porous portion and having an interior chamber in fluid communication with a perfusion lumen extending along the length of said catheter shaft from at least one perfusion port positioned within said interior of said flow control member to an external perfusion pump located outside the patient's aorta wherein said at least one perfusion port is sized and configured to expand said flow control member to a size sufficient to occlude a patient's aorta and to provide adequate flow to the arch vessels through said porous portion to sustain the metabolic demands of the brain; and at least one auxiliary flow control member coupled to said catheter shaft; and a corporeal perfusion lumen having a distal end and configured to reside inside the internal lumen of the patient's aorta when placed in an operative position and a proximal portion extending outside the body lumen of the patient configured for being coupled to said external perfusion pump and of sufficient size and internal diameter to communicate fluid from said external perfusion pump to at least one corporeal perfusion port to sustain the metabolic demands of the corporeal body.

14. The aortic catheter of claim 13, wherein said porous portion comprises one or more porous windows.

15. The catheter of claim 13, wherein said porous portion has a deployed diameter less than the deployed diameter of said occlusive end.

16. The catheter of claim 13, wherein a known rate of perfusion can be established by adjusting the pressure within the flow control member.

17. The catheter of claim 13, further comprising at least one auxiliary flow control member coupled to said elongated catheter distal to said flow control member.

18. The catheter of claim 13, further comprising at least one auxiliary flow control member coupled to said elongated catheter proximal to said flow control member.

19. The catheter of claim 13, wherein said porous portion comprises a filter.

20. The catheter of claim 13, wherein said porous portion is comprised of a filter material.

21. The catheter of claim 13, wherein said one or more porous window comprises a filter.

22. An aortic catheter comprising:

an elongated catheter shaft configured for introduction into a patient's aorta and having a proximal end and a distal end; and a flow control assembly coupled to said elongated catheter shaft having at least one expanded diameter sufficient to block blood flow through the aortic arch when deployed;

said flow control assembly comprising at least one porous inflatable member, whereby a fluid used to inflate said at least one porous inflatable member perfuses at a known rate through said at least one porous inflatable member to perfuse the arch vessels;

wherein said flow control assembly comprises two porous inflatable members, including a distal porous inflatable member and a proximal porous inflatable member, wherein said distal porous inflatable member has a nonporous distal side and a porous proximal side, and wherein said proximal porous inflatable member has a nonporous proximal side and a porous distal side.

23. A catheter for perfusing a branch lumen connected to a first body lumen in a patient comprising:

an elongated catheter shaft configured for introduction into the first body lumen of the patient, said catheter shaft having a proximal end and a distal end;

a flow control member coupled to said elongated catheter shaft having an expanded diameter sufficient to block blood flow through the first body lumen when deployed, said flow control member comprising a distal impermeable portion, a middle portion, and a proximal impermeable portion, said middle portion comprising a porous section, whereby a fluid used to inflate said middle portion perfuses through said porous section to perfuse the branch lumen; and at least one auxiliary flow control member coupled to said elongated catheter shaft.

24. The catheter of claim 23, wherein said at least one auxiliary flow control member comprises an inflatable balloon.

25. The catheter of claim 23, wherein said at least one auxiliary flow control member comprises a flow control valve.

26. The catheter of claim 23, wherein said at least one auxiliary flow control member is coupled to said elongated catheter shaft distal to said flow control member.

27. The catheter of claim 23, wherein said at least one auxiliary flow control member is coupled to said elongated catheter shaft proximal to said flow control member.

28. The catheter of claim 23, wherein said catheter comprises two auxiliary flow control members, including a first auxiliary flow control member coupled to said elongated catheter shaft proximal to said flow control member and a second auxiliary flow control member coupled to said elongated catheter shaft distal to said flow control member.

29. The catheter of claim 28, wherein said first and second auxiliary flow control members comprise inflatable balloons.

30. The catheter of claim 28, wherein said first and second auxiliary flow control members comprise flow control valves.

31. A catheter for perfusing a branch lumen connected to a first body lumen in a patient comprising:

an elongated catheter shaft configured for introduction into the first body lumen of the patient, said catheter shaft having a proximal end and a distal end; and a flow control member coupled to said elongated catheter shaft having an expanded diameter sufficient to block blood flow through the first body lumen when deployed, said flow control member comprising a distal impermeable portion, a middle portion, and a proximal impermeable portion, wherein said middle portion is configured with a window of porous material positioned on one side of said middle portion.

32. The catheter of claim 31, further comprising an inflatable balloon positioned within said flow control member.

33. The catheter of claim 32, wherein said inflatable balloon has a fully inflated state in which said inflatable balloon occludes fluid flow through said window of porous material.

34. A catheter for perfusing a branch lumen connected to a first body lumen in a patient comprising:

an elongated catheter shaft configured for introduction into the first body lumen of the patient, said catheter shaft having a proximal end and a distal end;

a distal porous inflatable member coupled to said elongated catheter shaft, wherein said distal porous inflatable member has a nonporous distal side and a porous proximal side; and a proximal porous inflatable member coupled to said elongated catheter shaft, wherein said proximal porous inflatable member has a nonporous proximal side and a porous distal side.

35. A catheter for perfusing a branch lumen connected to a first body lumen in a patient comprising:

an elongated catheter shaft configured for introduction into the first body lumen of the patient, said catheter shaft having a proximal end and a distal end; and a flow control member coupled to said elongated catheter shaft having an expanded diameter sufficient to block blood flow through the first body lumen when deployed, said flow control member comprising a distal impermeable portion, a middle portion, and a proximal impermeable portion, said middle portion comprising a porous section, whereby a fluid used to inflate said middle portion perfuses through said porous section to perfuse the branch lumen;

wherein said porous section is configured as a plurality of windows of porous material.

36. An aortic catheter comprising:

an elongated catheter shaft configured for introduction into a patient's aorta and having a proximal end and a distal end; and a flow control assembly coupled to said elongated catheter shaft having at least one expanded diameter sufficient to block blood flow through the aortic arch when deployed;

said flow control assembly comprising at least one porous inflatable member, whereby a fluid used to inflate said at least one porous inflatable member perfuses at a known rate through said at least one porous inflatable member to perfuse the arch vessels;

wherein said at least one porous inflatable member is configured with a plurality of windows of porous material.

* * * * *